US008031923B2

(12) United States Patent
Schummers et al.

(10) Patent No.: US 8,031,923 B2
(45) Date of Patent: Oct. 4, 2011

(54) METHOD, DEVICE AND COMPUTER PROGRAM PRODUCT FOR EVALUATING MEDICAL IMAGE DATA SETS

(75) Inventors: Georg Schummers, Munich (DE);
Marcus Schreckenberg, Freising (DE);
Dieter Bayer, Unterschleißheim (DE);
Horst Joachim Mayer, Munich (DE)

(73) Assignee: Tomtec Imaging Systems GmbH (DE)

( * ) Notice: Subject to any disclaimer, the term of this patent is extended or adjusted under 35 U.S.C. 154(b) by 1010 days.

(21) Appl. No.: 11/873,509

(22) Filed: Oct. 17, 2007

(65) Prior Publication Data

US 2008/0199062 A1 Aug. 21, 2008

(30) Foreign Application Priority Data

Oct. 19, 2006 (DE) .................. 10 2006 049 309

(51) Int. Cl.
*G06K 9/00* (2006.01)
(52) U.S. Cl. ...................................... 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| 2002/0126884 A1* | 9/2002 | Gerritsen et al. ............. 382/131 |
| 2004/0127794 A1* | 7/2004 | Murashita ..................... 600/442 |
| 2004/0249270 A1 | 12/2004 | Kondo et al. |
| 2005/0267366 A1* | 12/2005 | Murashita et al. ............. 600/437 |
| 2006/0018548 A1* | 1/2006 | Chen et al. .................... 382/190 |
| 2006/0049358 A1 | 3/2006 | Oumi et al. |

* cited by examiner

*Primary Examiner* — Samir Ahmed
*Assistant Examiner* — Atiba Fitzpatrick
(74) *Attorney, Agent, or Firm* — Cantor Colburn LLP

(57) ABSTRACT

The present invention relates to a method, a device and a computer program product for evaluating medical image data sets, which consists of two-dimensional section images, in particular MR images, wherein a plurality of two-dimensional cross-sections (K1, K2, . . . Kn) and at least one two-dimensional longitudinal section (L1) of a target region (1) of a human or animal body are recorded and stored, a longitudinal axis (5) and points of intersection (6) are determined at the points at which the longitudinal axis (5) extends through the plurality of two-dimensional cross-sections (K1, K2 . . . Kn) and a reduced data volume (7) is generated, which is composed of partial cross-sections (k1, k2, . . . kn), which are generated by means of the points of intersection (6) and scaling factors (a1, a2, b1, b2) from the plurality of two-dimensional cross-sections (K1, K2, . . . Kn).

14 Claims, 3 Drawing Sheets

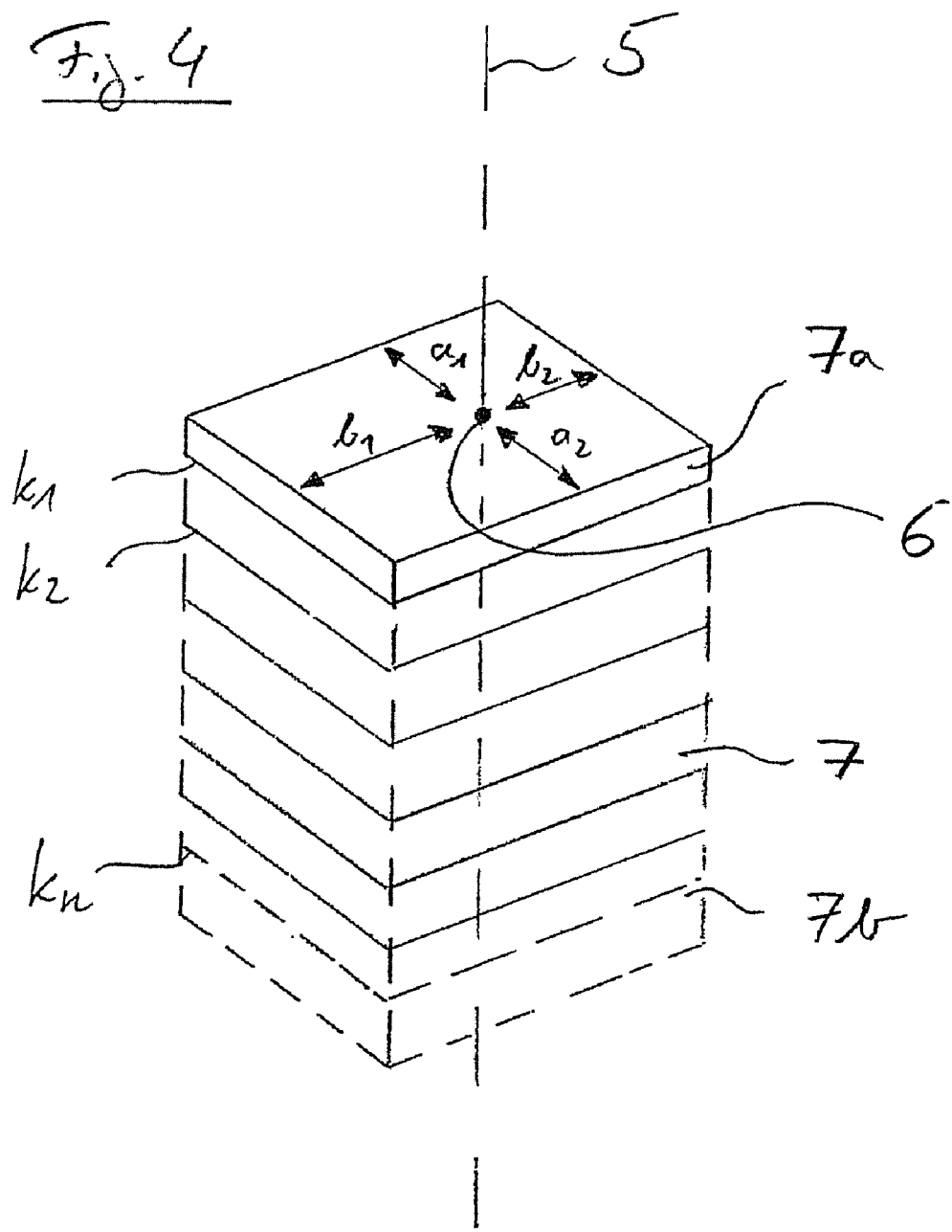

Figure 1:
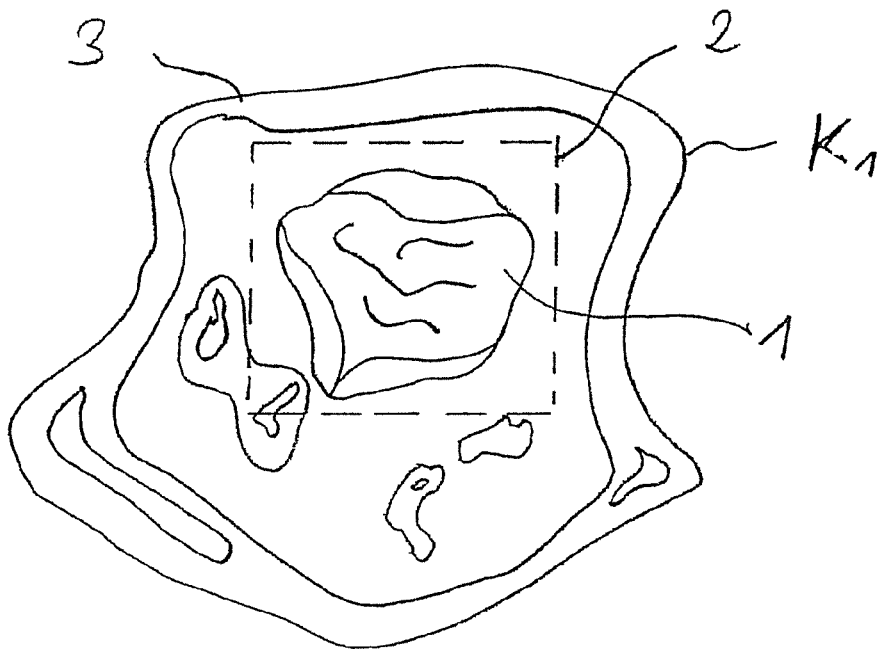

METHOD, DEVICE AND COMPUTER PROGRAM PRODUCT FOR EVALUATING MEDICAL IMAGE DATA SETS

The present invention relates to a method of evaluating medical image data sets consisting of two-dimensional section images, in particular MR images, and to a corresponding device according to claims 1 and 8 and a computer program product which contains a program code and is used to carry out the method.

Methods of this type are known in the prior art, wherein two-dimensional section images of an area of interest within the human or an animal body are generated by a medical image recording method and are reconstructed in a data set. The two-dimensional section images are suitable in particular for the three- or four-dimensional reconstruction of an organ, such as the human or an animal heart for example. In this case, currently modern image-generating methods are used which permit the acquisition of static or dynamic three-dimensional images, e.g. ultrasound, magnetic resonance tomography (MRT), positron emission tomography (PET), single photon emission computer tomography (SPECT) or computer tomography (CT). The term "dynamic" is intended to mean that a time sequence of two-dimensional images of the same organ is acquired at different moments in time, which permits visualisation of e.g. the movement of the heart.

Some of these medical image-generating methods, such as magnetic resonance tomography (MRT) for example, have the disadvantage, however, that due to memory limitation in current software or due to the recording method itself, rather than the organ itself being examined direct, e.g. the whole thorax of a human being must be recorded even though only a partial area, e.g. the left ventricle of the heart, is of interest. Conventional evaluation methods in this case generally use the original images which can be displayed on the screen and processed. On these images, however, far more can be seen than appears necessary for the diagnosis. Focusing on the target region which is of interest is usually only possible manually and by means of a series of approximation stages.

Furthermore, it is often difficult to reconstruct the whole body of a human or animal in full, since existing operating systems are not set up for this. An example data set (e.g. twelve two-dimensional cross-sections through the body and three two-dimensional longitudinal sections for 40 phases at 256×256 pixels per image) requires about 82 MB of memory for full reconstruction in order to represent each phase. The complete image data set therefore requires over 3.2 GB, although possibly only a small partial area, such as part of the heart for example, is of interest.

Particularly in the case of special pictures such as magnetic resonance tomography, focusing on the heart of the person is not possible. Therefore the full anatomy of the thorax is recorded, so that the target region, such as for example the heart, can only be found by complete three-dimensional reconstruction and by means of the underlying record protocol. In this case, the diagnosing doctor still often has to apply himself to the task.

Thus in conventional evaluation methods of medical image data sets of MR images in particular it is not possible to reconstruct these completely and reconstruction of the two-dimensional cross-sections often fails to permit any evaluation of the apex or valve region, because this region is not always recognisable due to movement of the heart through the plane of the image, and also because the heart valve for example is too thin.

Conventional evaluation methods therefore do not allow direct recognition of the spatial associations, but these are only detectable by reconstruction. Furthermore, the representation of individual section images by the reconstructed three-dimensional image data set is complicated and expensive since in each case a large amount of data has to be processed and displayed.

The object of the present invention is therefore to indicate a method of evaluating medical image data sets and to propose a corresponding device which makes available a reduced data set which is precisely tailored to the target region and makes available to the diagnosing doctor direct and at high speed section images which are cut through the area of interest.

Furthermore, it is an object of the present invention to reduce the memory requirement in the evaluation and representation of such image data sets and to make it easier for the doctor to navigate through the corresponding data sets in order to visualise these.

The object of the present invention is achieved by the independent claims 1, 8 and 12. Advantageous embodiments of the invention will appear from the subclaims and are claimed therein.

The method according to the invention for evaluating medical image data sets consisting of two-dimensional section images, in particular MR images, comprises the following steps:

1. A plurality of two-dimensional cross-sections and at least one two-dimensional longitudinal section of a target region of a human or animal body are taken and stored (as was also customary hitherto) by means of a medical image-generating method.
2. A longitudinal axis extending through the plurality of two-dimensional cross-sections is determined.
3. The points of intersection at which the longitudinal axis intersects with the two-dimensional cross-sections are determined.
4. Partial cross-sections are generated by cutting out segments from the two-dimensional cross-sections, these segments being determined by means of the points of intersection and scaling factors.
5. A reduced data volume is generated which is composed of the partial cross-sections.

The reduced data volume obtained is considerably smaller than a data volume which would be produced by the three-dimensional reconstruction of the two-dimensional cross-sections extending over a region which is far larger than the target region.

Advantageously, the longitudinal axis is determined by means of the at least one two-dimensional longitudinal section. According to a particularly preferred embodiment of the present invention, at least two two-dimensional longitudinal sections are determined, and the longitudinal axis is then fixed with the aid of these two longitudinal sections in such a manner that it either extends parallel to or on the straight section lines of these two two-dimensional longitudinal sections.

According to a further advantageous embodiment of the invention, a longitudinal axis is fixed by forming from a plurality of straight section lines of plural two-dimensional longitudinal sections a geometric centre, which according to the computing rule contains the data of a large number of or of all longitudinal sections. Selectively, a special straight section line of two longitudinal sections can determine the longitudinal axis by selection of the straight section line which has a predetermined angle to the planes of the preferably parallel, two-dimensional cross-sections.

The partial cross-sections for generating the reduced data volume may be circular segments which are thus produced from the respective two-dimensional cross-sections by selecting the circular segments of the corresponding point of intersection as the centre point of the circle, whilst as a scaling factor a predetermined radius is used.

According to another embodiment of the present invention, the partial cross-sections may also be rectangular segments of the respective two-dimensional cross-sections, the respective distances of the edges of the rectangular segments from the point of intersection being used as the scaling factor.

For representing and examining a human or animal body, the method uses the reduced data volume which is composed of the partial cross-sections, so that the doctor can lay his cuts rapidly due to the reduced data volume, in order to be able to look at section images of interest in the data volume. The rotation, cutting open, colouring or the moving view of a correspondingly reduced data volume is considerably quicker than the same actions in the use of a data volume which has been generated by means of the two-dimensional cross-sections.

The device according to the invention for evaluating medical image data sets consisting of two-dimensional section images, has memory means which store a plurality of two-dimensional cross-sections taken by means of a medical image-generating method, two-dimensional cross-sections and at least one two-dimensional longitudinal section of a target region of a human or animal body, and has processing means which determine a longitudinal axis extending through the plurality of two-dimensional cross-sections. The processing means furthermore determine the points of intersection at which the longitudinal axis intersects with the two-dimensional cross-sections. In this case, it is advantageous if the longitudinal axis intersects with as many as possible, in particular with all the two-dimensional cross-sections in order to be able to evaluate the entire volume. The processing means finally generate a reduced data volume composed of partial cross-sections which are generated by means of the points of intersection and any scaling factors from the plurality of two-dimensional cross-sections. These scaling factors can be determined in advance by concentrating on the object to be examined.

If for example the left ventricle of a heart is recorded as an image, then scaling factors are suitable which cut out circular or elliptical segments from the plurality of two-dimensional cross-sections, so that these circular or elliptical partial cross-sections produce a cylindrical or cylinder-like reduced data set. Alternatively, in taking an image of the head of a human or animal, scaling factors can be used which vary from one cross-section to another, e.g. a radius starting from the value 0 can be selected which depends in each case on the point of intersection of the longitudinal axis and the two-dimensional cross-sections, this radius increasing progressively and decreasing again until it has once more reached the value 0. In this case, a roughly spherical reduced data volume is obtained, with which tumours or carcinomas can be better represented.

The processing means according to the invention advantageously have means of selecting the partial cross-sections, the means of selecting determining circular or rectangular, elliptical or star-shaped segments of the respective two-dimensional cross-sections by means of the respective points of intersection. Furthermore, the device according to the invention advantageously has display means which use the reduced data volume to represent the target region of a human or animal body.

Furthermore, the invention also comprises a computer program product, which contains a stored program code on a computer-readable medium, this code carrying out the method according to the invention if the program code is carried out on a computer. As soon as the reduced data volume is indicated, the doctor can dissect the data volume by means of known graphics tools, cut out partial views or select and rotate three-dimensional views.

Figure 2:
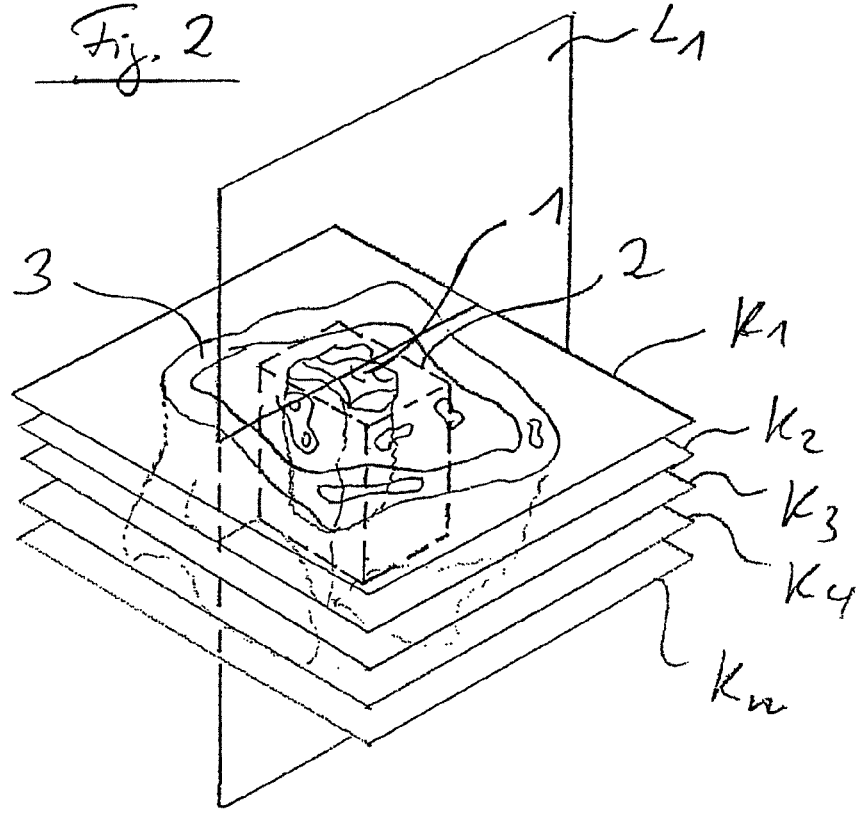

A preferred embodiment of the present invention is explained more fully with the aid of the attached drawings, which show:

FIG. 1 a two-dimensional cross-section through the entire region,

FIG. 2 the schematic representation of a plurality of two-dimensional cross-sections and one two-dimensional longitudinal section through the region, FIG. 3 the schematic representation of a plurality of two-dimensional cross-sections with three two-dimensional longitudinal sections and—shown in broken lines—the reduced data volume with additional areas lying above and below the stack of cross-sections, and FIG. 4 the reduced data volume with partial cross-sections and longitudinal axis.

FIG. 1 shows a two-dimensional cross-section through a recorded object 3, i.e. the entire region of an area within a human or animal body, such as for example the thorax of a patient. Within the object 3 lies the target region 1, which is defined by an area of interest 2. Hitherto, the doctor had to go to much trouble to determine the area of interest 2 manually and generate the individual section images there, and the data processing programs required a relatively long time to make the required views and data available.

FIG. 2 shows a plurality of two-dimensional cross-sections K1, K2, K3, K4, ... Kn, which, spaced apart, cut the object 3 transversely and represent corresponding layer images of a medical image-generating process, such as for example MR images of a magnetic resonance tomographer. Furthermore, FIG. 2 shows the two-dimensional longitudinal section L1 through the object 3, this longitudinal section also cutting the target region 1 within the area of interest 2.

Localising of the target region 1 is effected in modern medical image-generating methods with the aid of a recording protocol. If for example a picture is acquired according to the AHA or ASE recommendation, i.e. the left ventricle of a heart is acquired according to one of the standard protocols, then two-dimensional cross-sections are generated which depend in their number on the size of heart, and three two-dimensional longitudinal sections which, if possible, should lie with rotational symmetry to one another and in the target region 1. The plurality of two-dimensional cross-sections is in this case also called the "short axis stack", whilst the longitudinal sections are often also known as "long axis sections".

The plurality of two-dimensional cross-sections is generally so acquired that the uppermost and bottommost layer are to be found in the apex plane and in the valve plane of the heart.

Figure 3:
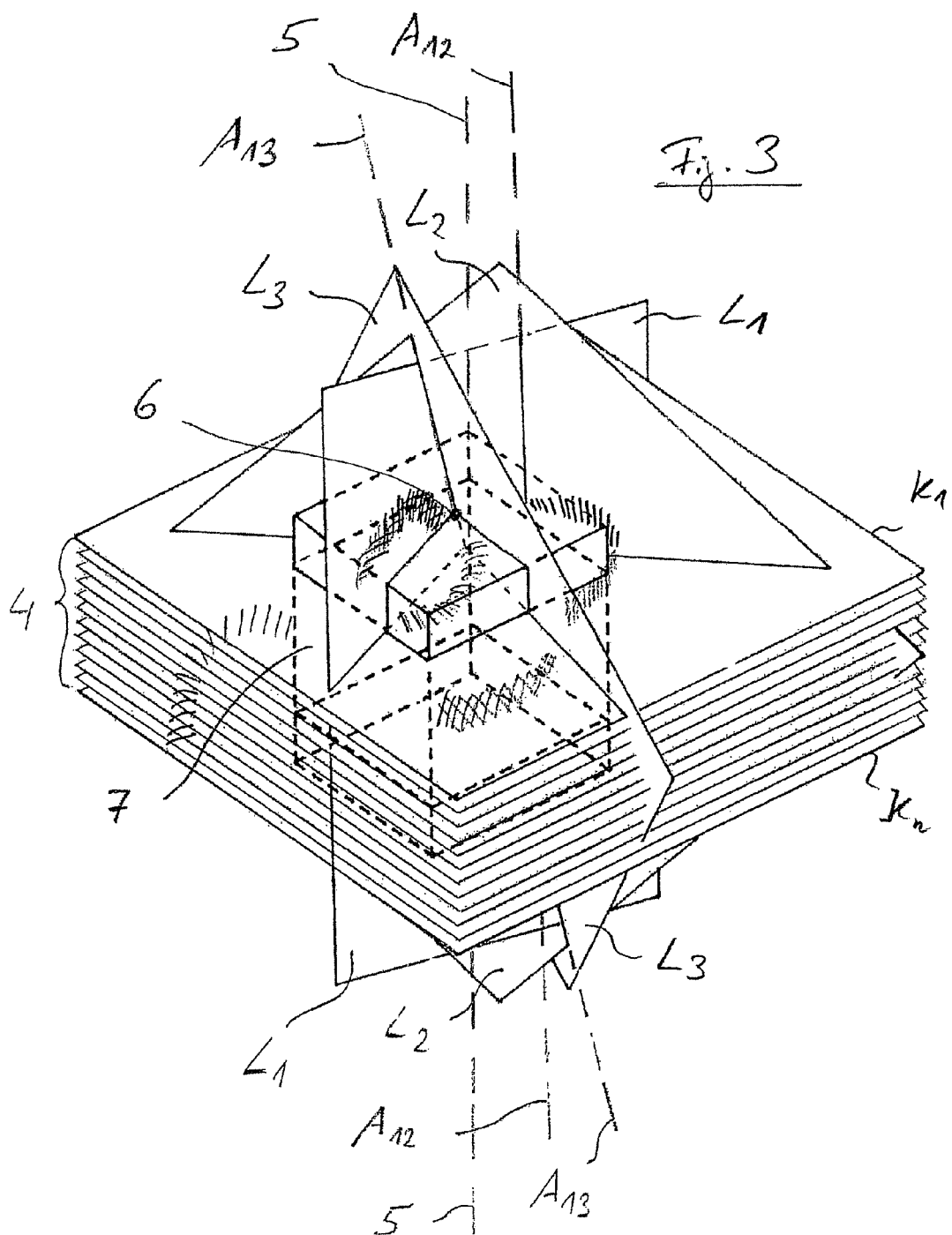

According to such a standard acquisition of a short axis stack 4 and of the corresponding three longitudinal sections, a data set is produced as is shown schematically in FIG. 3. A number of cross-sections K1, K2, ... Kn lie spaced apart substantially equidistant from one another and parallel to one another and form the short axis stack 4. This short axis stack 4 is intersected by a first longitudinal section L1, a second longitudinal section L2 not parallel thereto, and a third longitudinal section L3 not parallel to either of the two previous longitudinal sections. Generally, the operator can assume that the longitudinal sections L1, L2 and L3 are "rotated" in the target region 1, i.e. all together have a common section axis, which then automatically becomes the longitudinal axis 5.

If however the longitudinal sections L1, L2, L3 do not intersect in a common axis, i.e. if in the acquisition of these two-dimensional longitudinal sections the rotation is not performed "cleanly", then a longitudinal axis 5 must be determined which is either fixed by the formation of a geometric centre or by selecting one of the longitudinal sections or by a combination of these possibilities. Depending on the acquisition protocol, a section axis of this type can also be selected which has a suitable angle to the short axis stack 4.

In the embodiment shown according to FIG. 3, the three longitudinal sections L1, L2 and L3 have not been cleanly rotated, so that the first straight section line A12 between the first and second longitudinal section is not congruent with the second straight section line A13 between the first longitudinal section L1 and the third longitudinal section L3. In this case, the longitudinal axis 5 can be determined by forming a geometric centre of the first straight section line A12, the second straight section line A13 and the third straight section line A23 (not shown) between the second longitudinal section L2 and the third longitudinal section L3.

The longitudinal axis 5 intersects with the first cross-section K1 at a point of intersection 6, which—as is shown in FIG. 3—by chance coincides with the point of intersection of the second straight section line A13 and the first cross-section K1.

The point of intersection 6 is determined for each cross-section K1, K2, . . . Kn; then, with the aid of scaling factors, a reduced data volume 7 is determined (drawn in broken lines in FIG. 3).

The reduced data volume 7 in this case advantageously projects above and below the short axis stack 4 in order in particular to represent the apex and valve region of the left ventricle of the heart recorded.

The upper first additional volume 7a shown in FIG. 4 and the lower second additional volume 7b can be generated by extrapolation of the three-dimensional structure which is produced from the reduced data volume, which is generated by the use of the partial cross-sections.

In FIG. 4, the partial cross-sections k1, k2, . . . kn are indicated within the reduced data volume 7. The data volume 7 extends in this case along the longitudinal axis 5 and has a roughly rectangular cross-section. To form this cross-section, the scaling factors a1, a2, b1 and b2 indicated in FIG. 4 are used, which in particular determine the segment edges of the partial cross-section, in this case measured from the point of intersection 6 and respectively perpendicular to the edges of the short axis stack 4.

The scaling factors can be fixed for the entire short axis stack 4 or for only partial areas, e.g. it is also possible to use for each partial cross-section individual or varied scaling factors. The scaling factors are in particular dependent on the structure to be examined, the resolution of the picture, the computing power of the data processing unit and its memory.

If then the data so cut are used for the reconstruction, further peripheral conditions may influence the reconstruction stage:

1. The short axis stack 4 may in this case fix the coordinate system for the new volume. This is indicated for example in FIGS. 3 and 4. This is advantageous, since thus the plurality of cross-sections can retain their original resolution if the number of voxels of the reduced data volume 7 is matched to the remaining number of pixels of the partial cross-sections k1, k2, . . . kn.
2. Over- or under-scanning is possible in the case of correspondingly changing memory requirement.
3. The two-dimensional longitudinal sections L1, L2, L3 can be computed in with an adjustable weighting into the already-reconstructed partial cross-sections, or into the reduced data volume 7.

With the present invention, a reduced data volume 7 can be represented which can be supplied almost completely from original data and which can be very easily navigated and visualised. The doctor immediately recognises the spatial associations and can have the views he requires represented rapidly, as the memory requirements for the data-processing unit are acceptable.

The invention claimed is:

1. Method of evaluating medical image data sets which include two-dimensional section images, in particular MR images, the method comprising:
   (a) a plurality of two-dimensional cross-sections and at least one two-dimensional longitudinal section of a target region of a human or animal body are recorded by means of a medical image-generating method and stored,
   (b) a longitudinal axis is determined, which extends through the plurality of two-dimensional cross-sections,
   (c) points of intersection are determined, at which the longitudinal axis intersects with the two-dimensional cross-sections, and
   (d) a reduced data volume is generated which is composed of partial cross-sections, which are generated by means of the points of intersection and scaling factors from the plurality of two-dimensional cross-sections.

2. Method according to claim 1, wherein the longitudinal axis is determined by means of the at least one two-dimensional longitudinal section.

3. Method according to claim 1, wherein at least two two-dimensional longitudinal sections are determined and the longitudinal axis extends parallel to or on the straight section lines of two two-dimensional longitudinal sections.

4. Method according to claim 1, wherein the longitudinal axis is determined by the formation of a geometric centre from a large number of straight section lines of plural two-dimensional longitudinal sections or by the selection of those straight section lines of two longitudinal sections which have a predetermined angle to the planes of the two-dimensional cross-sections.

5. Method according to claim 1, wherein the partial cross-sections are circular segments of the respective two-dimensional cross-sections, whose respective centre point is the corresponding point of intersection, a predetermined radius being used as a scaling factor.

6. Method according to claim 1, wherein the partial cross-sections are rectangular segments of the respective two-dimensional cross-sections, wherein the respective distances of the edges of the rectangular segments from the point of intersection are used as scaling factors.

7. Method according to claim 1, wherein in order to represent and examine the target region of a human or animal body the reduced data volume is used, which is composed of the partial cross-sections.

8. Device for evaluating medical image data sets, which include two-dimensional section images, in particular MR images, comprising:
   (a) a memory means store a plurality of two-dimensional cross-sections recorded by means of a medical image-generating method and at least one two-dimensional longitudinal section of a target region of a human or animal body, (b) a processing means determine a longitudinal axis which extends through the plurality of two-dimensional cross-sections, (c) the processing means determine points of intersection at which the longitudinal axis intersects with the two-dimensional cross-sections, and (d) the processing means generate a reduced data volume composed of partial cross-sections which are generated by means of the points of intersection (6) and scaling factors from the plurality of two-dimensional cross-sections.

9. Device according to claim 8, wherein the processing means have means for selecting the partial cross-sections, the means of selection determining circular or rectangular segments of the respective two-dimensional cross-sections by means of the respective points of intersection.

10. Device according to claim 8, wherein the display means use the reduced data volume which is composed of the partial cross-sections in order to represent the target region of a human or animal body.

11. Method according to claim 4, wherein the planes of the two-dimensional cross-sections are parallel.

12. Computer program product, which contains a program code stored on a non-transitory computer-readable medium and which carries out the method according to one of claim 1 to 7 or 11 if the program code is carried out on a computer.

13. Device which is suitable for carrying out a method according to claim 1-7 or 11.

14. Device according to claim 9, wherein the display means use the reduced data volume which is composed of the partial cross-sections in order to represent the tar region of a human or animal body.

\* \* \* \* \*